United States Patent [19]

Urbahns et al.

[11] Patent Number: 5,646,166
[45] Date of Patent: Jul. 8, 1997

[54] USE OF 5-ACYL-1,4-DIHYDROPYRIDINES

[75] Inventors: Klaus Urbahns, Wuppertal; Hans-Georg Heine, Krefeld; Thomas Glaser, Overath; Reilinde Wittka, Köln; Jean-Marie-Viktor De Vry, Rösrath; Henning Sommermeyer, Köln, all of Germany

[73] Assignee: Bayer Aktiengesellschaft, Leverkusen, Germany

[21] Appl. No.: 569,438

[22] Filed: Dec. 8, 1995

[30] Foreign Application Priority Data

Dec. 16, 1994 [DE] Germany ............ 44 44 864.3

[51] Int. Cl.$^6$ .................................. A61K 31/44
[52] U.S. Cl. .......................... 514/355; 514/356
[58] Field of Search ..................... 514/355, 356

[56] References Cited

U.S. PATENT DOCUMENTS

| 3,966,948 | 6/1976 | Bossert et al. ............... 424/266 |
| 5,446,057 | 8/1995 | Augelli-Szafran et al. ............ 514/356 |

FOREIGN PATENT DOCUMENTS

| 0406502 | 1/1991 | European Pat. Off. . |
| 0675409 | 10/1995 | European Pat. Off. . |
| 2018738 | 10/1971 | Germany . |
| 2018739 | 10/1971 | Germany . |
| 2302866 | 8/1973 | Germany . |

OTHER PUBLICATIONS

V.K. Lusis, et al., Chem. Het. Compounds (Engl. Translation), vol. 19, pp. 415–419, (1983).
P.W.L. Tas, et al., Neuroscience Letters, vol. 94, pp. 279–284, (1988).

*Primary Examiner*—Theodore J. Criares
*Attorney, Agent, or Firm*—Sprung Horn Kramer & Woods

[57] ABSTRACT

The present invention relates to the new use of 1-alkyl-3,5-diacyl-1,4-dihydropyridines which are known in some cases, of the general formula (I)

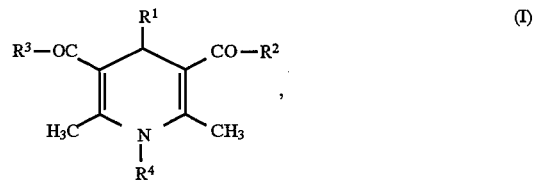

in which $R^1$ to $R^4$ have the meaning indicated in the description, processes for their preparation and their use as medicaments, as selective potassium channel modulators, in particular for the treatment of the central nervous system.

4 Claims, No Drawings

USE OF 5-ACYL-1,4-DIHYDROPYRIDINES

The present invention relates to the new use of 1-alkyl-3,5-diacyl-1,4-dihydropyridines which are known in some cases, processes for their preparation and their use as medicaments, as selective potassium channel modulators, in particular for the treatment of the central nervous system.

Acyl-1,4-dihydropyridines having circulatory action are disclosed in the publications DOS (German Offenlegungsschrift) 20 18 738 and 20 18 739 and U.S. Pat. No. 3,966,948.

A few 4-aryl-2,6-dimethyl-3,5-diacetyl-1,4-dihydropyridines are additionally described as synthetic building blocks in the publication Chem. Het. Compounds (Engl. Transl.), Vol. 19, 1983, part 4, pp. 415–419=Khim. Geterosikl. Soedin Vol. 4, 1983, pp. 508–513.

It has now been found that the 1-alkyl-5-acyl-1,4dihydropyridines which are known in some cases, of the general formula (I)

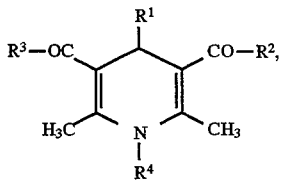

in which
R$^1$ represents aryl having 6 to 10 carbon atoms, which is optionally substituted up to 5 times by identical or different nitro, cyano, halogen or trifluoromethyl substituents or by straight-chain or branched alkylthio having up to 6 carbon atoms, R$^2$ and R$^3$ are identical or different and each represent straight-chain or branched alkyl having up to 8 carbon atoms or phenyl, or R$^2$ represents straight-chain or branched alkoxy having up to 8 carbon atoms or phenoxy, and R$^4$ represents straight-chain or branched alkyl having up to 4 carbon atoms, surprisingly have a selective modulating action on potassium channels and are suitable for use in the control of disorders of the central nervous system and sickle cell anemia.

The compounds according to the invention can exist in stereoisomeric forms which either behave as image and mirror image (enantiomers), or which do not behave as image and mirror image (diastereomers). The invention relates both to the antipodes and to the racemic forms as well as the diastereomer mixtures. Like the diastereomers, the racemic form can also be separated into the stereoisomerically uniform constituents in a known manner.

Preferably used compounds of the general formula (I) are those
in which
R$^1$ represents phenyl or naphthyl, each of which is optionally substituted up to 3 times by identical or different nitro, cyano, fluorine, chlorine, bromine, iodine or trifluoromethyl substituents or by straight-chain or branched alkylthio having up to 4 carbon atoms, R$^2$ and R$^3$ are identical or different and each represent straight-chain or branched alkyl having up to 6 carbon atoms or phenyl, or R$^2$ represents straight-chain or branched alkoxy having up to 6 carbon atoms or phenoxy, and R$^4$ represents straight-chain or branched alkyl having up to 4 carbon atoms, in the control of disorders of the central nervous system.

Particularly preferably used compounds of the general formula (I) are those
in which
R$^1$ represents phenyl which is optionally substituted up to 3 times by identical or different nitro, cyano, fluorine, chlorine, bromine, iodine or trifluoromethyl substituents or by methylthio, R$^2$ and R$^3$ are identical or different and each represent alkyl having up to 4 carbon atoms or phenyl, or R$^2$ represents alkoxy having up to 4 carbon atoms or phenoxy, and R$^4$ represents methyl or ethyl, in the control of disorders of the central nervous system.

The compounds of the general formula (I) according to the invention show an unforeseeable, useful spectrum of pharmacological action.

They are channel modulators having a surprising selectivity for calcium-dependent potassium channels of high conductivity (BK(Ca) channels), in particular the potassium channels of the central nervous system.

On account of their pharmacological properties, they can be employed for the production of medicaments for the treatment of degenerative central nervous system disorders, such as e.g. on occurrence of dementias (multiinfarct dementia (MID), primary degenerative dementia (PDD), pre- and senile Alzheimer's disease, HIV dementia and other forms of dementia), Parkinson's disease or amyotropic lateral sclerosis and also multiple sclerosis.

The active compounds are furthermore suitable for the treatment of brain function disorders in the aged, of organic brain syndrome (OBS) and of age-related memory disorders (age-associated memory impairment, AAMI).

They are suitable for the prophylaxis, treatment and for the control of the sequelae of cerebral circulatory disorders such as cerebral ischaemias, strokes, craniocerebral traumata and of subarachnoid haemorrhages.

They are useful for the treatment of depressions and psychoses, e.g. schizophrenia. They are additionally suitable for the treatment of disorders of neuroendocrine secretion and of neurotransmitter secretion and health disorders associated therewith such as mania, alcoholism, drug abuse, dependence or abnormal eating behaviour. Further application areas are the treatment of migraine, sleep disorders and of neuropathies. They are moreover suitable as analgesics.

The active compounds are furthermore suitable for the treatment of disorders of the immune system, in particular of T-lymphocyte proliferation and for affecting the smooth musculature, in particular of uterus, urinary bladder and bronchial tract, and for the treatment of diseases associated therewith such as e.g. asthma and urinary incontinence and for the treatment of arrhythmia, angina and diabetes.

The invention additionally relates to new selected compounds of the general formula (I), having the substituent meanings indicated in the following table:

| R$^1$ | R$^2$ | R$^3$ | R$^4$ |
|---|---|---|---|
| 2,4,5-Cl-C$_6$H$_2$ | CH$_3$ | CH$_3$ | CH$_3$ |
| 2,3,5-Cl-C$_6$H$_2$ | CH$_3$ | CH$_3$ | CH$_3$ |
| 3,4,5-F$_3$—C$_6$H$_2$ | CH$_3$ | CH$_3$ | CH$_3$ |
| 2,3-Cl-C$_6$H$_3$ | CH$_3$ | CH$_3$ | CH$_3$ |
| 4-Cl-C$_6$H$_4$ | CH$_3$ | CH$_3$ | CH$_3$ |
| 3,4-Cl-C$_6$H$_3$ | CH$_3$ | CH$_3$ | CH$_3$ |
| 4-F—C$_6$H$_4$ | CH$_3$ | CH$_3$ | CH$_3$ |
| 4-Cl-C$_6$H$_4$ | OCH$_3$ | —CH$_3$ | —CH$_3$ |

-continued

| R¹ | R² | R³ | R⁴ |
|---|---|---|---|
| 2,3-Cl-C₆H₃ | OCH₃ | —CH₃ | —CH₃ |
| 3-NO₂—C₆H₄ | OCH₃ | —CH₃ | —CH₃ |
| 3,4,5-F—C₆H₂ | OCH₃ | —CH₃ | —CH₃ |
| 4-F—C₆H₄ | OCH₃ | —CH₃ | —CH₃ |
| 3,4-Cl-C₆H₃ | OCH₃ | —CH₃ | —CH₃ |
| 4-NO₂—C₆H₄ | OCH₃ | —CH₃ | —CH₃ |
| 3-CF₃, 4-Cl-C₆H₂ | OCH₃ | —CH₃ | —CH₃ |

The compounds of the formula (I) according to the invention can be prepared by

A) reacting aldehydes of the general formula (II)

   (II)

in which
R¹ has the meaning indicated above,
with β-keto compounds of the general formula (III)

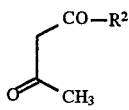   (IIIa)

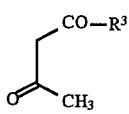   (IIIb)

in which
and R² and R³ have the meaning indicated above,
and with alkylamine hydrochlorides in inert solvents,
if appropriate in the presence of a base, or B) reacting aldehydes of the formula (II) with β-keto compounds of the formula (IIIa) and enamines of the formula (IV)

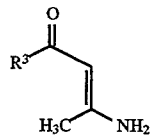   (IV)

in which
R³ has the meaning indicated above,
first to give 1,4-dihydropyridines of the general formula (V)

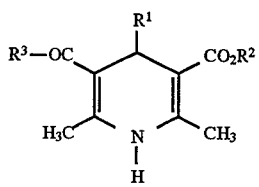   (V)

in which
R¹, R² and R³ have the meaning indicated above,
in inert solvents,
and then reacting these with alkylating agents of the general formula (VI)

   (VI)

in which
R⁴ has the meaning indicated above and
L represents halogen, preferably bromine or iodine, if appropriate under a protective gas atmosphere, in inert solvents and in the presence of a base.

The processes according to the invention can be illustrated by way of example by the following reaction scheme:

A)

B)

Suitable solvents are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether, or diethylene glycol dimethyl ether, acetonitrile, acetone or amides such as hexamethylphosphoramide or dimethylformamide, or halogenated hydrocarbons such as methylene chloride, carbon tetrachloride, or hydrocarbons such as benzene or toluene, or pyridine. It is also possible to use mixtures of the solvents mentioned. Pyridine is preferred for process (A) and isopropanol for process (B).

The reaction temperatures can be varied within a relatively wide range. In general, the reaction is carried out between +10° C. and +150° C., preferably between +20° C. and 100° C., in particular at the boiling point of the respective solvent.

The reactions can be carried out at normal pressure, but also at elevated or reduced pressure (e.g. 0.5 to 3 bar). In general, the reactions are carried out at normal pressure. Suitable solvents for the alkylation are in general customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoramide, acetonitrile, acetone or nitromethane. It is also possible to use mixtures of the solvents mentioned. Dimethylformamide is preferred.

Suitable bases for the alkylation are in general alkali metal alkoxides such as sodium or potassium methoxide, sodium or potassium ethoxide or potassium tert-butoxide. It is also possible to employ alkali metals such as sodium or their hydrides such as sodium hydride as bases. Sodium hydride is preferred.

The alkylation is in general carried out using alkylating agents such as, for example, ($C_1$-$C_4$)-alkyl halides, sulphonic acid esters or substituted or unsubstituted ($C_1$-$C_4$)-dialkyl sulphates, preferably methyl iodide or dimethyl sulphate.

The alkylation is in general carried out in one of the abovementioned solvents, preferably in dimethylformamide, in a temperature range from 0° C. to +70° C., preferably from 0° C. to +30° C. and at normal pressure.

When carrying out the process according to the invention, any desired ratio of the substances participating in the reaction can be used. In general, however, the process is carried out with molar amounts of the reactants.

The compounds of the general formulae (II), (III), (IV) and (V) are known or can be prepared by known methods.

Enantiomerically pure forms are obtained e.g. by separating diastereomer mixtures of the compounds of the general formula (I), in which $R^2$ represents an optically active ester radical, according to a customary method, then either transesterifying directly or first preparing the chiral carboxylic acids and then preparing the enantiomerically pure dihydropyridines by esterification.

In general, the diastereomers are separated either by fractional crystallization, by column chromatography or by countercurrent distribution. Which is the optimum process must be decided from case to case, sometimes it is also expedient to use combinations of the individual processes. Separation by crystallization or countercurrent distribution or a combination of both processes is particularly suitable.

The enantiomerically pure compounds are accessible, inter alia, by chromatography of the racemic esters on chiral phases.

The compounds of the general formula (I) according to the invention show an unforeseeable spectrum of action, in particular on account of their selectivity for calcium-dependent potassium channels of high conductivity.

[86]Rubidium efflux from C6-BU1 glioma cells

The experiments were carried out with slight modifications according to the method described by Tas et al. (Neurosci. Lett. 94, 279–284, (1988)). To do this, C6-BU1 glioma cells from rats are used. From the data obtained by liquid scintillation, the increase in the efflux produced by ionomycin above the basal efflux is calculated and set as 100 %. The stimulations in the presence of test substances are then related to this value.

The present invention also includes pharmaceutical preparations which, in addition to inert, non-toxic, pharmaceutically suitable auxiliaries and excipients, contain one or more compounds of the general formula (I), or which consist of one or more active compounds of the formula (I), and processes for the production of these preparations.

The active compounds of the formula (I) should be present in these preparations in a concentration of 0.1 to 99.5% by weight, preferably of 0.5 to 95% by weight of the total mixture.

In addition to the active compounds of the formula (I), the pharmaceutical preparations can also contain other pharmaceutical active compounds.

The abovementioned pharmaceutical preparations can be prepared in a customary manner by known methods, for example using the auxiliary(ies) or excipient(s).

In general, it has proven advantageous to administer the active compound(s) of the formula (I) in total amounts of about 0.01 to about 100 mg/kg, preferably in total amounts of about 1 mg/kg to 50 mg/kg of body weight every 24 hours, if appropriate in the form of several individual doses, to achieve the desired result.

However, if appropriate it may be advantageous to depart from the amounts mentioned, namely depending upon the type and the body weight of the subject treated, on individual behaviour towards the medicament, the nature and severity of the disorder, the type of preparation and administration, and the time or interval at which administration takes place.

Starting Compounds

EXAMPLE I

Methyl 5-acetyl-2,6-dimethyl-4-(4-chlorophenyl)-1, 4-dihydropyridine-3-carboxylate

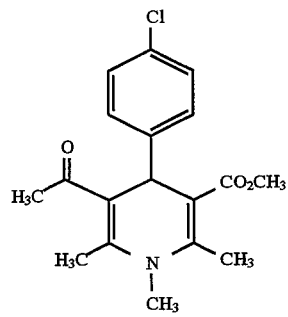

5.64 g (40 mmol) of 4-chlorobenzaldehyde, 4.0 g (40 mmol) of 4-aminopent-3-en-2-one and 4.6 g (40 mmol) of methyl acetoacetate are heated to reflux for 12 h in 100 ml of isopropanol. The reaction mixture is allowed to cool and is concentrated. 1.85 g of the title compound crystallize from $Et_2O$.

Preparation Examples

EXAMPLE 1

1-[5-Acetyl-4-(2,4,5-trichlorophenyl)-1,2,6-trimethyl-1,4-dihydropyridin-3-yl]ethanone

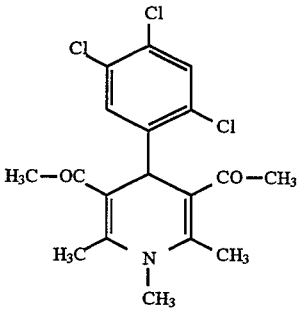

5.0 g (23.9 mmol) of 2,4,5-trichlorobenzaldehyde, 4.8 g (47.8 mmol) of acetylacetone and 1.78 g (26.3 mmol) of methylamine hydrochloride are boiled under reflux for 5 h in 4 ml of pyridine. The pyridine is then stripped off and the residue is codistilled twice with toluene. It is taken up in AcOEt and the solution is extracted with 1N aqueous HCl. Drying and concentration of the aqueous phase yields a brown oil, which is purified by flash chromatography (petroleum ether/AcOEt=5:1). The product is finally recrystallized from ether. 4.2 g of the title compound (45% of theory) are obtained. MS:385 $R_f$=0.65 (petroleum ether: AcOEt:=1:1)

The compounds listed in Table 1 are prepared in analogy to the procedure of Example 1:

TABLE 1

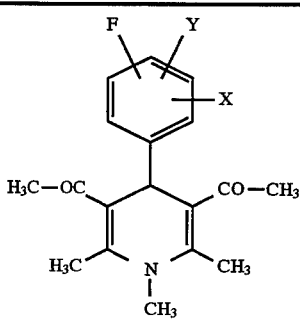

| Ex. No. | X | Y | Z | Yield (% of theory) | MS | $R_f$* |
|---|---|---|---|---|---|---|
| 2 | 2-Cl | 3-Cl | 5-Cl | 30 | 385 | 0.64 |
| 3 | 3-F | 4-F | 5-F | 33 | 337 | 0.43 |
| 4 | 2-Cl | 3-Cl | 4-H | 17 | 351 | 0.39 |
| 5 | 4-Cl | 3-H | 2-H | 20 | 317 | 0.40 |
| 6 | 2-H | 3-Cl | 4-Cl | 27 | 351 | 0.38 |
| 7 | H | H | 4-F | 16 | 301 | 0.41 |

*= petroleum ether/AcOEt = 1:1

EXAMPLE 8

Methyl 5-acetyl-4-(4-chlorophenyl)-1,2,6-trimethyl-1,4-dihydropyridine-3-carboxylate

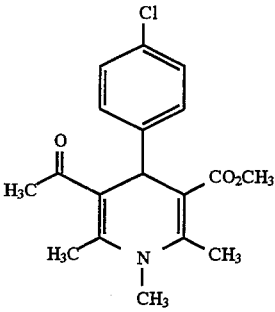

1.0 g (3.2 mmol) of the compound from Example I are dissolved in 15 ml of DMF and treated under argon with 180 mg of NaH. The mixture is stirred at 0° C. for 15 minutes. 0.51 ml (6.2 mmol) of MeI is then added dropwise and the mixture is stirred again for 30 min. It is treated successively with $H_2O$ and ethyl acetate and the organic phase is washed with saturated aqueous NaCl solution. It is then concentrated and the residue is separated on silica gel (petroleum ether/ AcOEt=1+1). The appropriate fractions crystallize from $Et_2O$/petroleum ether. 230 mg of the title compound are obtained. MS:333.8 $R_f$=0.57 (petroleum ether/AcOEt=1+1)

The compounds listed in Table 2 are prepared in analogy to the procedure of Example 8:

TABLE 2

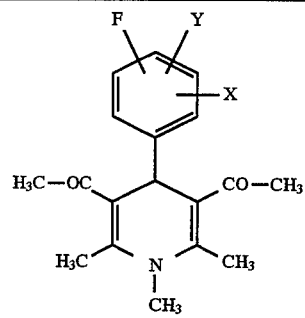

| Ex. No. | X/Y/Z | Yield (% of theory) | $R_f$ (PE/AcOEt 1:1) | MS |
|---|---|---|---|---|
| 9 | 2,3-Cl/4-H | 37 | 0.43 | 367 |
| 10 | 2-H, 3-$NO_2$ | 66 | 0.41 | 344 |
| 11 | 3,4,5-F | 10 | 0.58 | 353 |
| 12 | 2-H, 3-H, 4-F | 14 | 0.55 | 317 |
| 13 | 2-H, 3-Cl, 4-Cl | 16 | 0.56 | 367 |
| 14 | 2-H, 3-H, 4-$NO_2$ | 32 | 0.39 | 344 |
| 15 | 2-H, 3-$CF_3$, 4-Cl | 20 | 0.52 | 401 |

We claim:

1. A method of treating a patient suffering from a disorder of the central nervous system that is responsive to a selective modulating action on potassium channels, said method comprising administering to said patient an effective amount therefor of a 1-alkyl-5-acyl-1,4-dihydropyridine of the formula (I):

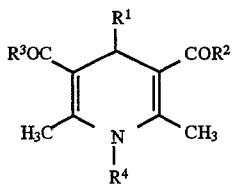

(I)

in which
R¹ represents aryl having 6 to 10 carbon atoms, which is optionally substituted up to 5 times by identical or different nitro, cyano, halogen or trifluoromethyl substituents or by straight-chain or branched alkylthio having up to 6 carbon atoms, R² and R³ are identical or different and each represent straight-chain or branched alkyl having up to 8 carbon atoms or phenyl, or R² represents straight-chain or branched alkoxy having up to 8 carbon atoms or phenoxy, and R⁴ represents straight-chain or branched alkyl having up to 4 carbon atoms.

2. Method of treatment according to claim 1, comprising administering a compound selected from the group consisting of:

1-[5-Acetyl-4-(2,4,5-trichlorophenyl)-1,2,6-trimethyl-1,4-dihydropyridin-3-yl]-ethanone;

1-[5-Acetyl-4-(2,3,5-trichlorophenyl)-1,2,6-trimethyl-1,4-dihydropyridin-3-yl]-ethanone;

1-[5-Acetyl-4-(3,4,5-trichlorophenyl)-1,2,6-trimethyl-1,4-dihydropyridin-3-yl]-ethanone;

1-[5-Acetyl-4-(2,3-dichlorophenyl)-1,2,6-trimethyl-1,4-dihydropyridin-3-yl]-ethanone;

1-[5-Acetyl-4-(4-chlorophenyl)-1,2,6-trimethyl-1,4-dihydropyridin-3-yl]-ethanone;

1-[5-Acetyl-4-(3,4-dichlorophenyl)-1,2,6-trimethyl-1,4-dihydropyridin-3-yl]-ethanone;

1-[5-Acetyl-4-(4-fluorophenyl)-1,2,6-trimethyl-1,4-dihydropyridin-3-yl]-ethanone;

Methyl 5-acetyl-4-(4-chlorophenyl)-1,2,6-trimethyl-1,4-dihydropyridine-3-carboxylate;

Methyl 5-acetyl-4-(2,3-dichlorophenyl)-1,2,6-trimethyl-1,4-dihydropyridine-3-carboxylate;

Methyl 5-acetyl-4-(3-nitrophenyl)-1,2,6-trimethyl-1,4-dihydropyridine-3-carboxylate;

Methyl 5-acetyl-4-(3,4,5-trifluorophenyl)-1,2,6-trimethyl-1,4-dihydropyridine- 3-carboxylate;

Methyl 5-acetyl-4-(4-fluorophenyl)-1,2,6-trimethyl-1,4-dihydropyridine-3-carboxylate;

Methyl 5-acetyl-4-(3,4-dichlorophenyl)-1,2,6-trimethyl-1,4-dihydropyridine-3-carboxylate;

Methyl 5-acetyl-4-(4-nitrophenyl)-1,2,6-trimethyl-1,4-dihydropyridine-3-carboxylate; and Methyl 5-acetyl-4-(4-chloro-3-trifluoromethylphenyl)-1,2,6-trimethyl-1,4-dihydropyridine-3-carboxylate.

3. Method of treatment according to claim 1, comprising administering a compound of formula (I), in which R¹ represents phenyl or naphthyl, each of which is optionally substituted up to 3 times by identical or different nitro, cyano, fluorine, chlorine, bromine, iodine or trifluoromethyl substituents or by straight-chain or branched alkylthio having up to 4 carbon atoms, R² and R³ are identical or different and each represent straight-chain or branched alkyl having up to 6 carbon atoms or phenyl, or R² represents straight-chain or branched alkoxy having up to 6 carbon atoms or phenoxy, and R4 represents straight-chain or branched alkyl having up to 4 carbon atoms.

4. Method of treatment according to claim 1, comprising administering a compound of formula (I), in which R¹ represents phenyl which is optionally substituted up to 3 times by identical or different nitro, cyano, fluorine, chlorine, bromine, iodine or trifluoromethyl substituents or by methylthio, R² and R³ are identical or different and each represent alkyl having up to 4 carbon atoms or phenyl, or R² represents alkoxy having up to 4 carbon atoms or phenoxy, and R⁴ represents methyl or ethyl.

* * * * *